(12) United States Patent
Noda et al.

(10) Patent No.: US 9,580,729 B2
(45) Date of Patent: Feb. 28, 2017

(54) METHOD FOR PRODUCING ETHANOL

(71) Applicants: Kansai Chemical Engineering Co., Ltd., Hyogo (JP); Bio-energy Corporation, Hyogo (JP)

(72) Inventors: Hideo Noda, Hyogo (JP); Shinji Hama, Hyogo (JP); Nobuyuki Kuratani, Hyogo (JP); Akihiko Kondo, Hyogo (JP)

(73) Assignees: KANSAI CHEMICAL ENGINEERING CO., LTD., Hyogo (JP); BIO-ENERGY CORPORATION, Hyogo (JP)

( * ) Notice: Subject to any disclaimer, the term of this patent is extended or adjusted under 35 U.S.C. 154(b) by 95 days.

(21) Appl. No.: 14/385,533

(22) PCT Filed: Mar. 21, 2013

(86) PCT No.: PCT/JP2013/058106
§ 371 (c)(1),
(2) Date: Sep. 16, 2014

(87) PCT Pub. No.: WO2013/146540
PCT Pub. Date: Oct. 3, 2013

(65) Prior Publication Data
US 2015/0037858 A1 Feb. 5, 2015

(30) Foreign Application Priority Data
Mar. 26, 2012 (JP) .................. 2012-069285

(51) Int. Cl.
C12P 7/10 (2006.01)
C12P 7/14 (2006.01)

(52) U.S. Cl.
CPC ...... *C12P 7/10* (2013.01); *C12P 7/14* (2013.01); *Y02E 50/16* (2013.01)

(58) Field of Classification Search
CPC ............... C12P 7/10; C12P 7/14; Y02E 50/16
See application file for complete search history.

(56) References Cited

U.S. PATENT DOCUMENTS 7,192,764 B2    3/2007   Fukuda et al.
2005/0089602 A1 4/2005   Kvist et al.
(Continued)

FOREIGN PATENT DOCUMENTS

EP   WO 2009/127729  * 10/2009
JP        11-290078     10/1999
(Continued)

OTHER PUBLICATIONS

Fujita et al., Direct and Efficient Production of Ethanol from Cellulosic Material with a Yeast Strain Displaying Celluloytic Enzymes, Applied and Environmental Microbiology (2002), vol. 68(10), pp. 5136-5141.*

(Continued)

*Primary Examiner* — Alexander Kim
(74) *Attorney, Agent, or Firm* — Ajay A. Jagtiani; Miles & Stockbridge P.C.

(57) ABSTRACT

A method for producing ethanol from lignocellulosic biomass using yeast at low cost is provided. The method of the present invention for producing ethanol from lignocellulosic biomass includes steps of (1) pretreating lignocellulosic biomass, (2) treating a cellulose fraction obtained in Step (1) with a cellulose hydrolase, (3) mixing saccharified biomass obtained in Step (2) with yeasts to perform ethanol fermentation, and (4) subjecting a fermentation product obtained in Step (3) to a solid-liquid separation, wherein a cycle consisting of Steps (1), (2), (3) and (4) is repeated twice or more, and yeasts obtained in Step (4) are used as all or a portion of yeasts in Step (3) of the subsequent cycle.

7 Claims, 3 Drawing Sheets

(56) References Cited

U.S. PATENT DOCUMENTS

| | | |
|---|---|---|
| 2006/0005279 A1 | 1/2006 | Dotson et al. |
| 2011/0183396 A1 | 7/2011 | Noda et al. |
| 2012/0252085 A1 | 10/2012 | Edwards et al. |

FOREIGN PATENT DOCUMENTS

| | | | |
|---|---|---|---|
| JP | 2004-520058 | | 7/2004 |
| JP | 2007-523646 | | 8/2007 |
| JP | 2010-17084 | | 1/2010 |
| JP | 2010-536389 | | 12/2010 |
| JP | 2011-41493 | | 3/2011 |
| JP | 2011-92041 | | 5/2011 |
| JP | 2011-142879 | A | 7/2011 |
| JP | 2011-0152079 | A | 8/2011 |
| WO | WO92/16615 | * | 10/1992 |
| WO | 02/085935 | A1 | 10/2002 |
| WO | 2010/032762 | A1 | 3/2010 |

OTHER PUBLICATIONS

Li et al., Evaluation of industrial *Saccharomyces cerevisiae* strains as the chassis cell for second-generation bioethanol production., Microbial Biotechnology (2015), John Wiley & Sons Ltd and Society for Applied Microbiology, pp. 266-274.*
Groves et al., Functional cell surface expression of the anion transport domain of human red cell band 3 (AE1) in the yeast *Saccharomyces cerevisiae*., Proc. Natl. Acad. Sci. USA (1996), vol. 93, pp. 12245-12250.*
Agilent Technologies (last viewed on Jun. 8, 2016), pp. 1-356.*
Basso et. al., Epub Sep. 15, 2011, pp. 85-100, Ethanol Production in Brazil: The Industrial Process and Its Impact on Yeast Fermentation, Biofuel Production—Recent Developments and Prospects, Dr. Marco Aurelio Dos Santos Bernardes (Ed.), ISBN: 978-953-307-478-8, InTech. http://www.intechopen.com/books/.*
Wong et al., Engineering *Saccharomyces cerevisiae* to produce feruloyl esterase for the release of ferulic acid from switchgrass., J Ind Microbiol Biotehcnol (2011), vol. 38, pp. 1961-1967.*
Domingues et al. (Aspergillus niger β-galactosidase production by yeast in a continuous high cell density reactor., Process Biochemistry (2005), vol. 40, pp. 1151-1154.*
Biofuels International (2011), Easy to digest enzymes., pp. 59-61.*
Sukumaran et al., Cellulase production using biomass feed stock and its application in lignocellulose saccharification for bio-ethanol production., Renewable Energy (2009), vol. 34, pp. 421-424.*
Wang et al., High-Temperature Enzymatic Breakdown of Cellulose., Applied and Environmental Microbiology (2011), vol. 77, pp. 5199-5206.*
International Search Report received in PCT/JP2013/058106.
Sanda et al., "Repeated-batch fermentation of lignocellulosic hydrolysate to ethanol u sing a hybrid *Saccharomyces cerevfisiae* strain metabolically engineered for tolerance to acetic and formic acids", Bioresource Technology, 102, pp. 7917-7924 (2011).

* cited by examiner

METHOD FOR PRODUCING ETHANOL

TECHNICAL FIELD

The present invention relates to a method for producing ethanol, and more specifically, to a method for producing ethanol from biomass.

BACKGROUND ART

Recently, since there is a concern that fossil fuels are feared to be exhausted, alternative fuels are being developed. In particular, bioethanol derived from biomass has attracted attention. This is because biomass is a renewable resource, which exists in large amounts on the earth, and can be used without increasing carbon dioxide in the air (carbon neutral) so as to contribute to the prevention of global warming.

However, bioethanol is produced mainly from corns or sugarcanes nowadays, and therefore, there is a problem in that bioethanol competes with food. Therefore, in the future, the production of bioethanol from lignocellulosic biomass such as rice straw, wheat straw, waste wood or the like that does not compete with food will be required.

The lignocellulosic biomass includes mainly three components that are cellulose, hemicellulose and lignin. Cellulose is decomposed (saccharified) into glucoses by hydrolysis, and thus, can be used in ethanol fermentation by a yeast *Saccharomyces cerevisiae* that can utilize glucose.

Cellulose hydrolases such as cellulase are generally used to hydrolyze cellulose, and a pretreatment for separating cellulose from biomass and exposing it is performed prior to the enzymatic reaction in order to facilitate the enzyme reacting with cellulose. Conventionally, a hydrothermal decomposition method, an acid treatment method and an alkaline treatment method have been known as the pretreatment. A method of using dilute acid in a high temperature (200° C. or higher) and a method of using concentrated sulfuric acid or the like are known as the acid treatment method. However, since cellulose is partially decomposed under severe conditions by the hydrothermal decomposition method or by the acid treatment method, there is a problem in that over-decomposed products (by-products) are produced, glucose yield (saccharification rate) is low, and substances that inhibit the ethanol fermentation can be also produced.

Lignocellulosic biomass pretreatment products are subjected to an enzymatic treatment. In the enzymatic treatment, a cellulose component and a hemicellulose component included in the pretreatment products are hydrolyzed to produce oligosaccharides and monosaccharides. However, since the potency of the commercially-available enzyme used in the saccharification is low and thus a large amount of the enzyme is needed for sufficient saccharification, there is a problem in that the cost is increased.

On the other hand, attempts have been made in which the yeast *Saccharomyces cerevisiae* or the like that cannot originally utilize cellulose, hemicellulose and the like is modified using a bioengineering technique to produce ethanol directly from the biomass pretreatment products. A cell surface display technique is used as such a bioengineering technique. For example, a yeast displaying the group of enzymes that hydrolyze cellulose, that is, endoglucanase, cellobiohydrolase, β-glucosidase and the like, on its surface is produced using the cell surface displaying technique (Patent Document 1).

CITATION LIST

Patent Documents

Patent Document 1: WO 2010/032762

SUMMARY OF THE INVENTION

Technical Problem

In view of industrial usefulness, an investigation is necessary a for improving the productivity of ethanol by combining the above-described methods. In particular, as an effective technique, a method has been examined in which the ethanol fermentation is performed using the yeast displaying the group of cellulose hydrolases on its cell surface while the saccharification of the lignocellulosic biomass pretreatment product is allowed to proceed to a certain extent by an enzymatic treatment method. However, in this method, yeasts need to be prepared and added every time when the fermentation is performed, and therefore, the cost of yeast culture greatly affects the cost of ethanol production.

It is an object of the present invention to provide a method for producing ethanol from lignocellulosic biomass using yeasts at low cost.

Solution to Problem

The inventors of the present invention have found that it is possible to produce ethanol from a lignocellulosic biomass at low cost by efficiently separating reusable yeasts from the fermentation products after the fermentation using a combination of solid-liquid separation steps, and have completed the present invention.

the present invention provides a method for producing ethanol from lignocellulosic biomass comprising steps of: (1) pretreating lignocellulosic biomass; (2) treating a cellulose fraction obtained in Step (1) with a cellulose hydrolase; (3) mixing saccharified biomass obtained in Step (2) with yeasts to perform ethanol fermentation; and (4) subjecting a fermentation product obtained in Step (3) to a solid-liquid separation, wherein a cycle consisting of Steps (1), (2), (3) and (4) is repeated twice or more, and yeasts obtained in Step (4) are used as all or a portion of yeasts in Step (3) of a subsequent cycle.

In one embodiment, the Step (4) comprises steps of: (a) removing a solid content constituting 5 to 30% by mass of the fermentation products; and (b) collecting a solid content constituting 5 to 30% by mass of residue obtained in Step (a).

In some embodiment, a concentration of yeast cells in the fermentation products is $10^7$ cells/mL or more.

In one embodiment, the yeast is transformed so as to express one or two enzymes selected from the group consisting of ferulic acid esterase, β-glucosidase, β-galactosidase and pectinase.

In one embodiment, the enzyme is displayed on a surface.

In one embodiment, the present invention provides a composition containing yeasts for producing ethanol from lignocellulosic biomass, wherein the yeasts are transformed so as to express one or two enzymes selected from the group consisting of ferulic acid esterase, β-glucosidase, β-galactosidase and pectinase.

In one embodiment, the enzyme is displayed on a surface.

Advantageous Effects of the Invention

With the method of the present invention, by using, in the subsequent fermentation cycle, a certain amount of residue containing yeasts after removing a residue having a high specific gravity from the fermentation products of ethanol fermentation using lignocellulosic biomass, it is possible to repeat fermentation cycles for a long period of time without additionally supplying yeasts while the concentration of yeast cells is maintained in a certain range of approximately $10^6$ to $10^7$ cells/mL to $10^7$ cells/mL or more. Since a yeast constantly repeats proliferation, there is no problem in that its freshness is reduced. Since the cost for preparing a new batch of yeasts can be reduced, it is possible to produce ethanol at low cost. Moreover, it is possible to prevent the residue with a high specific gravity from inhibiting fermentation.

DESCRIPTION OF EMBODIMENTS

Figure 1:
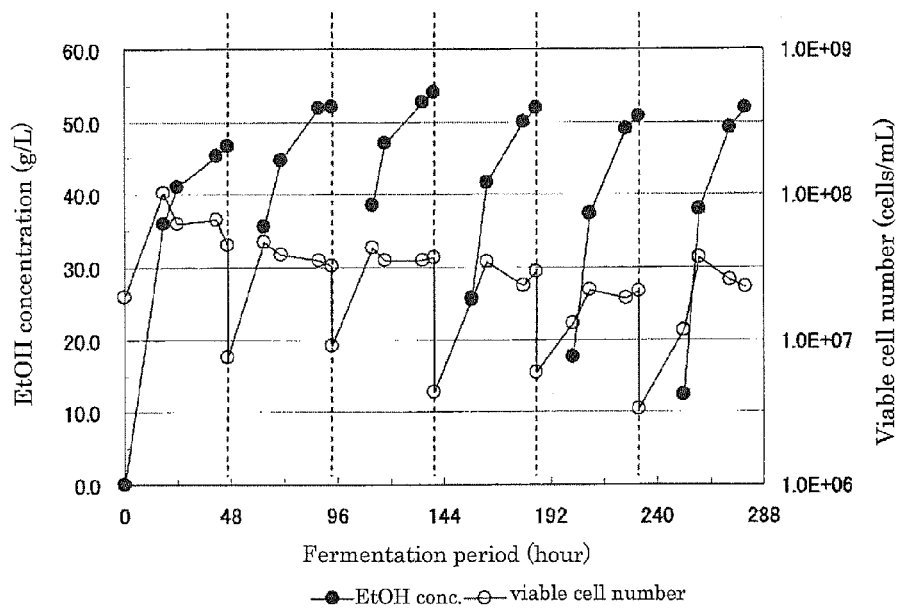
FIG. 1 is a graph illustrating time course in the concentrations of ethanol and yeast cells in fermentation liquid in the case where rice straw was used as raw materials to perform ethanol fermentation with yeasts being repeatedly reused.

The method of the present invention for producing ethanol from lignocellulosic biomass includes steps of (1) pretreating lignocellulosic biomass, (2) treating a cellulose fraction obtained in Step (1) with a cellulose hydrolase, (3) mixing saccharified biomass obtained in Step (2) with yeasts to perform ethanol fermentation, and (4) subjecting a fermentation product obtained in Step (3) to a solid-liquid separation.

(1) Pretreatment of Lignocellulosic Biomass (Step (1))

Biomass is a saccharine material derived from biological resources. Examples thereof include starch obtained from corns or the like and molasses (blackstrap molasses) obtained from sugar canes or the like. Lignocellulosic biomass is biomass including mainly three components that are cellulose, hemicellulose and lignin. Cellulose is a fibrous macromolecule in which glucopyranoses (glucoses) are polymerized by β-1,4-glucosidic bonds, and glucoses obtained by hydrolyzing cellulose are used as a fermentation substrate for yeasts and the like.

The use of lignocellulosic biomass is preferable in that it does not compete with food. Examples of the lignocellulosic biomass include waste products produced when a biological material such as rice, wheat, corn, sugar cane, wood (pulp), and napier grass is treated. Examples of the waste products include rice straw, wheat straw, bagasse (residue after squeezing sugar canes), and waste wood.

The pretreatment is a treatment in which cellulose is separated from biomass and is exposed prior to the enzymatic reaction, such as the treatment with a cellulose hydrolase such as cellulase for hydrolyzing cellulose into glucoses, in order to facilitate the enzyme reacting with cellulose. The pretreatment is not limited. Examples thereof include a hydrothermal decomposition method, and a squeezing and steaming method.

In the hydrothermal decomposition method, for example, lignocellulosic biomass is pulverized as needed and thus is mixed with water so that a content of the biomass is approximately 20% by mass (dry mass), for example, and the mixture is subjected to a thermal treatment. The thermal treatment is performed at 120 to 300° C., preferably at 150 to 280° C., and more preferably at 180 to 250° C., for 15 seconds to 1 hour. A temperature and a period of time of the treatment can be varied depending on the type of biomass to be used, and an increase in the temperature of treatment can shorten the period of time of the treatment. It should be noted that the mixture may be pressurized during the thermal treatment.

In the squeezing and steaming method, lignocellulosic biomass is squeezed and steamed. There is no particular limitation on the order of squeezing and steaming, and a person skilled in the art can set the order thereof as appropriate. Examples of the squeezing method include, but are not particularly limited to, a method for squeezing lignocellulosic biomass with a hydraulic squeezing machine, a screw press, a meat separator, a press dehydrator, a centrifuge, or the like. Examples of the steaming method include, but are not particularly limited to, a method for steaming lignocellulosic biomass with high-temperature steam. Examples of the steaming conditions include, but are not particularly limited to, conditions in which lignocellulosic biomass is impregnated with sulfuric acid that is 1 to 5% by mass with respect to the lignocellulosic biomass and is steamed under a pressure of 1.0 to 1.6 MPa at 180 to 200° C. for 5 to 30 minutes.

When lignocellulosic biomass is pretreated, a water-soluble hemicellulose fraction and a water-insoluble cellulose fraction are separated. The water-insoluble cellulose fraction can be easily separated as a solid content by centrifugation or the like. In this step, the cellulose fraction can be obtained from the lignocellulosic biomass. A solid content in the cellulose fraction is preferably 100 g dry weight/L or more, and more preferably 200 g dry weight/L or more, but is not particularly limited thereto.

(2) Treatment of Cellulose Fraction Obtained in Step (1) with a Cellulose Hydrolase (Step (2))

A cellulose hydrolase hydrolyzes β-1,4-glucoside bonds in cellulose to produce glucoses. This process is called saccharification. Examples of the cellulose hydrolase include, but are not limited to, endo-β-1,4-glucanase (referred to as merely "endoglucanase" hereinafter), cellobiohydrolase and β-glucosidase.

The endoglucanase is an enzyme also called cellulase and cleaves cellulose intramolecularly to produce glucoses, cellobioses and cellooligosaccharides (the degree of polymerization is 3 or more and generally 10 or less, but is not limited thereto). The endoglucanase has a high reactivity to cellulose with a low crystallinity or non-crystalline cellulose, for example, non-cystallized cellulose, soluble cellooligosaccharide and a cellulose derivative such as carboxymethyl cellulose (CMC), but has a low reactivity to cellulose microfibril having a crystalline structure. The endoglucanase is an example of the enzyme that hydrolyzes non-crystalline cellulose. Examples of the endoglucanase include, but are not limited to, endoglucanase derived from *Trichoderma reesei* (in particular, EGII).

The cellobiohydrolase hydrolyzes cellulose from its reducing terminal or its non-reducing terminal to produce cellobioses. The cellobiohydrolase hydrolyzes crystalline cellulose such as cellulose microfibril having a crystalline structure, but has a low reactivity to cellulose with a low crystallinity or non-crystalline cellulose, for example, a cellulose derivative such as carboxymethyl cellulose (CMC). The cellobiohydrolase is an example of the enzyme that hydrolyzes crystalline cellulose. The rate of hydrolysis of crystalline cellulose by the cellobiohydrolase is smaller than the rate of hydrolysis of non-crystalline cellulose by endoglucanase due to a strong structure by intermolecular and intramolecular dense hydrogen bonds of crystalline cellulose. There are two types of cellobiohydrolase, which are called cellobiohydrolase 1 and cellobiohydrolase 2 respectively. Examples of the cellobiohydrolase include, but are not limited to, cellobiohydrolase derived from *Trichoderma reesei* (in particular, CBH2).

The β-glucosidase is an exo-type hydrolase that separates a glucose unit from the non-reducing terminal in cellulose. The β-glucosidase cleaves a β-1,4-glucoside bond between an aglycone or a sugar chain and β-D-glucose, and hydrolyzes cellobiose or cellooligosaccharide to produce glucose. The β-glucosidase is an example of an enzyme that hydrolyzes cellobiose or cellooligosaccharide. Nowadays, one type of β-glucosidase is known and is called β-glucosidase 1. Examples of the β-glucosidase include, but are not limited to, β-glucosidase derived from *Aspergillus aculeatus* (in particular, BGL1).

There is no limitation on a cellulose hydrolase preparation as long as the preparation contains any of the above-described cellulose hydrolases. The preparation may be a commercially available preparation or a preparation prepared from cultivated microorganisms producing those enzymes. The activity of the cellulose hydrolase is expressed as the amount of the enzyme that separates 1 μmol of glucose from filter paper (Filter Paper: No. 1 filter manufactured by Whatman, for example) for 1 minute (1FPU). The concentration of the cellulose hydrolase used in the treatment is preferably 4 to 20 FPU/g cellulose fraction, but is not particularly limited thereto. The period of time of the treatment by the cellulose hydrolase is preferably 0.5 to 10 hours, more preferably 0.5 to 8 hours, and even more preferably 0.5 to 6 hours, but is not particularly limited thereto. There is no particular limitation on a temperature in the treatment by the cellulose hydrolase as long as the enzyme can act. The temperature is preferably 40 to 80° C.

In this step, it is possible to obtain saccharified biomass from the cellulose fraction. The saccharified biomass is biomass obtained by a saccharification treatment, and contains, as a main component, glucose (monosaccharide) produced by hydrolysis of cellulose, for example. Examples of the form of the saccharified biomass include, but are not particularly limited to, a slurry form.

In this step, a nutrient source for a yeast may be added. Examples of the nutrient source for a yeast include, but are not particularly limited to, YP (containing 10 g/L of yeast extract and 20 g/L of polypeptone), corn steep liquor (CSL) and a combination thereof, and corn steep liquor is preferable. Since the corn steep liquor is inexpensive, it is possible to reduce the cost of ethanol fermentation. There is no particular limitation on the amount of the nutrient source for a yeast added. For example, in the case of adding YP, the amount thereof may be any amount between 1×YP to 10×YP, and, for example, 5 mL of YP is added with respect to approximately 48 mL of the total amount of the enzymatic treatment solution. For example, in the case of adding corn steep liquor, the content of the corn steep liquor with respect to the total amount (mL) of the enzymatic treatment solution prepared in, for example, the treatment of the cellulose fraction by a cellulose hydrolase is, for example, 0.05 to 2% by mass, preferably 0.0625 to 1% by mass, and more preferably 0.125 to 0.5% by mass. There is no particular limitation on the timing for adding the nutrient source for a yeast, and the nutrient source may be added before or after the treatment of the cellulose fraction by a cellulose hydrolase or during the treatment.

(3) Ethanol Fermentation by Mixing Saccharified Biomass Obtained in Step (2) and Yeasts (Step (3))

There is no particular limitation on a yeast as long as the yeast can utilize glucose as a substrate for ethanol fermentation. The yeast may be a wild-type yeast or a transformed yeast. The transformed yeast is produced as appropriate by a method generally used by a person skilled in the art.

The yeast is preferably a yeast belonging to the genus *Saccharomyces*, and more preferably *Saccharomyces cerevisiae*, but is not particularly limited thereto. Examples of the strain of *Saccharomyces cerevisiae* include *Saccharomyces cerevisiae* TJ14 (Moukamnerd et. al., Appl. Microbiol. Biotechnol., 2010, vol. 88, p. 87-94) and *Saccharomyces cerevisiae* KF-7 (Ting et. al., Process Biochem., 2006, vol. 41, p. 909-914).

The transformed yeast can be a yeast that, for example, expresses the enzyme for promoting the saccharification of lignocellulosic biomass by the cellulose hydrolase preparation in Step (2). Examples of such an enzyme include, but are not particularly limited to, ferulic acid esterase, β-glucosidase, β-galactosidase, pectinase, and a combination of one or two of these enzymes. The yeast transformed so as to express ferulic acid esterase is preferable.

The ferulic acid esterase is an enzyme that causes an esterification reaction between ferulic acid and glycerol. The ferulic acid esterase exhibits an effect of hydrolyzing ferulic acid that connects lignin to polysaccharide in lignocellulosic biomass. This function allows the structure of the lignocellulosic biomass to be loosened (that is, a portion of the structure of the lignocellulosic biomass to be decomposed), and thereby, it is possible to promote the saccharification by the cellulose hydrolase preparation. Examples of the ferulic acid esterase include, but are not particularly limited to, ferulic acid esterases derived from the genera *Aspergillus* (e.g., *Aspergillus niger*), *Penicillium* (e.g., *Penicillium chrysogenum*), and *Talaromyces* (e.g., *Talaromyces funiculosus*). Examples of a gene coding for ferulic acid esterase include the gene derived from *Talaromyces funiculosus* (FaeA: GenBank Accession Number: AJ312296).

The pectinase is a collective term for the group of enzymes that decompose pectic substances contained in cell walls of the higher plants. Examples of the pectinase include, but are not particularly limited to, pectinases derived from bacteria belonging to the genus *Bacillus*, yeasts belonging to the genera *Tricosporon, Endomyces, Endomycopsis, Saccharomyces, Schizosaccharomyces, Pichia, Hansenula, Debaryomyces, Hanseniaspora, Torulopsis, Candida* and *Kluyveromyces*, and filamentous fungi belonging to the genera *Aspergillus* and *Rhizopus*.

The above-described β-glucosidase can be used as the β-glucosidase.

The β-galactosidase is an enzyme that decomposes lactose to galactose and glucose. The β-galactosidase exhibits an effect of decomposing galactan in pectin and loosening the structure of a plant cell wall (that is, decomposing a portion of the structure of lignocellulosic biomass). It is expected that this allows lignocellulosic biomass to be softened and thus promotes the saccharification by the cellulose hydrolase preparation. Examples of the β-galactosidase include, but are not particularly limited to, β-galactosidases derived from the genera *Bacillus* (e.g., *Bacillus circulars*) and *Aspergillus* (e.g., *Aspergillus oryzae*).

The gene coding for the above-described enzyme can be obtained by, for example, amplifying the gene by a polymerase chain reaction (PCR) using the genome DNA or cDNA, as a template, prepared from the organism from which the enzyme is derived and a pair of primers produced based on the sequence information of its structural gene.

The above-described enzyme may be expressed, for example, so as to be secreted from the yeast or be displayed on the yeast surface.

In the present invention, a method known to a person skilled in the art can be adopted as the method for displaying the enzyme on the yeast cell surface, and, for example, a GPI anchor (Japanese Laid-Open Patent Publication No. H11-290078) or a sugar chain-binding domain (WO 02/085935) of a cell-surface localized protein can be used. Examples of the cell-surface localized protein used in these methods include α- or a-agglutinin (flocculation protein of yeasts), FLO protein (e.g., FLO1, FLO2, FLO4, FLO5, FLO9, FLO10 and FLO11) and alkaline phosphatase.

Examples of the method for displaying the enzyme on the cell surface using the GPI anchor include a method using a recombinant DNA constituted of a secretion signal sequence-coding DNA, a target gene, and a GPI anchor attachment recognition signal-coding DNA. Glucoamylase that is expressed from this recombinant DNA and is secreted outside the cell membrane can be bound to the GPI anchor of the cell membrane via the GPI anchor attachment recognition signal. A GPI anchor attachment recognition signal sequence that exists in the sequence of 320 amino acids from the C-terminus of yeast α-agglutinin can be used as the GPI anchor attachment recognition signal sequence.

Examples of the method for displaying the enzyme on the cell surface using the sugar chain-binding domain include a method using a recombinant DNA in which the enzyme is bound to the N-terminus, C-terminus or both N-terminus and C-terminus of the cell-surface localized protein (flocculation functional domain). The enzyme that is expressed from this recombinant DNA and is secreted outside the cell membrane can stay on the cell surface because a plurality of sugar chains in the sugar chain-binding domain interact with the sugar chains in the cell wall. Examples of the flocculation functional domain include a sugar chain-binding site of lectin, lectin-like protein or the like, and typically the flocculation functional domain of the GPI anchor protein.

The secretion signal sequence used in the recombinant DNA may be a secretion signal of the enzyme, a secretion signal sequence of the cell-surface localized protein, or another secretion signal sequence capable of leading the enzyme outside the cell, but is not particularly limited thereto. A portion or all of the secretion signal sequence and pro-sequence may remain in the N-terminus after the cell surface display as long as there is no influence on the enzyme activity.

In the present invention, the method for secreting the enzyme from a yeast can be performed, for example, by introducing, to a yeast, the recombinant DNA in which the gene coding for the target enzyme is linked to the downstream of the DNA coding for the above-described secretion signal sequence.

The synthesis and linkage of the above-described recombinant DNA can be performed, for example, by a method generally used by a person skilled in the art.

The above-described recombinant DNA may be incorporated into an expression vector. Such an expression vector is, for example, a plasmid form. For example, a plasmid having the replication origin (Ori) of the yeast 2 μm plasmid and the replication origin of ColE1 is preferably used. It is preferable that the plasmid has a selective marker and a replication gene for *Escherichia coli* in that the plasmid preparation and the detection of transformant are facilitated. Examples of the selective marker include a drug resistance gene and an auxotrophic gene. Examples of the drug resistance gene include, but are not particularly limited to, the ampicillin resistance gene (Ampr) and the kanamycin resistance gene (Kanr). Examples of the auxotrophic gene include, but are not particularly limited to, the N-(5'-phosphoribosyl)anthranilate isomerase (TRP1) gene, tryptophan synthase (TRP5) gene, β-isopropylmalate dehydrogenase (LEU2) gene, imidazoleglycerol-phosphate dehydrogenase (HIS3) gene, histidinol dehydrogenase (HIS4) gene, dihydroorotate dehydrogenase (URA1) gene and orotidine-5-phosphate decarboxylase (URA3) gene. A replication gene for a yeast is selected as needed.

It is preferable that the expression vector has a promoter and a terminator suitable for expressing the gene coding for a target enzyme in a yeast. Examples of the promoter and the terminator include, but are not particularly limited to, the promoter and the terminator of GAPDH (glyceraldehyde 3'-phosphate dehydrogenase), PGK (phosphoglycerate kinase), PYK (pyruvate kinase) and TPI (triosephosphate isomerase). The gene coding for a target enzyme is inserted between the promoter and the terminator.

There is no particular limitation on the method for introducing the recombinant DNA into a yeast. Examples thereof include a lithium acetate method, an electroporation method and a protoplast method. The introduced recombinant DNA may exist, for example, in a plasmid form, or in a form in which the recombinant DNA is inserted into the yeast chromosome or is incorporated into the yeast chromosome by a homologous recombination.

A yeast into which the recombinant DNA has been introduced is selected by the selectable marker and by measuring the activity of the expressed enzyme. For example, an antibody against the enzyme can be used to confirm that the target enzyme is displayed on the cell surface.

There is no particular limitation on the concentration of yeast cells at the start of the first fermentation. It is preferably approximately 2 to 20 g wet weight/L ($1 \times 10^7$ to $1 \times 10^8$ cells/mL). There is no particular limitation on the conditions of yeast culture. Generally, the conditions may be conditions when performing ethanol fermentation using glucose as a substrate. The culture temperature is 30 to 37° C., for example. The culture pH is 4 to 8, for example.

In the method of the present invention, the period of time of fermentation can be made short, and therefore, the period of time of the culture is generally 2 to 3 days. The end of the fermentation is determined based on the fact that the amount of carbon dioxide gas produced becomes a tenth or less of that at the start of the fermentation for example.

(4) Solid-Liquid Separation of Fermentation Products Obtained in Step (3) (Step (4))

Fermentation products after finishing the fermentation contain yeasts and ethanol produced during the fermentation as well as solid content such as lignin and an ash content derived from the raw material. That is, a slurry containing a solid content is also encompassed. The concentration of yeast cells in the fermentation products after finishing the fermentation is $1 \times 10^7$ to $5 \times 10^8$ cells/mL, preferably $5 \times 10^7$ to $5 \times 10^8$ cells/mL, and more preferably $1 \times 10^8$ to $5 \times 10^8$ cells/mL in the case where the concentration of yeast cells at the start of the first fermentation is approximately $1 \times 10^7$ to $5 \times 10^8$ cells/mL, for example, but is not particularly limited thereto. Yeasts is efficiently collected from the fermentation products using a combination of the solid-liquid separation steps, and thus is reused. The combination of the solid-liquid separation steps is preferably a combination of (a) a step of removing a solid content of 5 to 30% by mass of the fermentation products (Step (4)(a)), and (b) a step of collecting a solid content of 5 to 30% by mass of the remaining portion obtained in Step (4)(a) (Step (4)(b)), but is not particularly limited thereto.

(a) Step of Removing a Solid Content of 5 to 30% by Mass of the Fermentation Products (Step (4)(a))

In this step, yeast is collected in a liquid portion. To do so, the solid content of 5 to 30% by mass, preferably 5 to 20% by mass of the fermentation products obtained in Step (3) is removed. Examples of a means for removing the solid content preferably include, but are not particularly limited to, a centrifugation at 100 to 1000 G, a hydrasieve and a decanter. In this step, most of the lignin and the ash content is removed as a solid content.

(b) Step of Collecting a Solid Content of 5 to 30% by Mass of the Remaining Portion Obtained in Step (4)(a) (Step (4)(b))

In this step, the yeast is collected in a solid content. a solid content of 5 to 30% by mass, preferably 20 to 30% by mass of the remaining portion obtained in Step (4)(a) is collected. Examples of a means for collecting the solid content preferably include, but are not particularly limited to, a centrifugation at 1200 to 5000 G, a filter press and an Oliver filter. In this step, most of ethanol produced during the fermentation is collected as a liquid portion.

The ratio of the collected yeast in Step (4) is preferably 50% or more, but is not particularly limited thereto. The ratio of the accompanying residue such as lignin and ash content and the like is preferably 10% or less, but is not particularly limited thereto.

In the method of the present invention, a cycle including the above-described Steps (1) to (4) is repeated twice or more, and preferably six times or more. Then, the yeast obtained in Step (4) is used as all or a portion of yeasts in Step (3) of the subsequent cycle. The ratio of the yeasts obtained in Step (4) with respect to yeasts used in Step (3) of the subsequent cycle is 50 to 100% by mass and preferably 80 to 100% by mass.

In the method of the present invention, additional supply of yeasts used in the fermentation can be reduced, and therefore, the cost can be reduced.

EXAMPLES

Hereinafter, the present invention will be specifically described by way of examples, but the present invention is not limited to the examples.

Example 1

Ethanol Fermentation Using Rice Straw 1

Step 1: Hydrothermal Treatment of Rice Straw

Rice straw was mixed with water so that the content thereof was approximately 20% by mass (dry mass). The mixture was put into a hydrothermal treatment device (manufactured by Mitsubishi Heavy Industries, Ltd.) and was treated at approximately 180° C. at approximately 3 MPa for 5 to 20 minutes. Next, a solid content was separated, and then, the separated solid content was used as a fermentation substrate.

Step 2: Enzymatic Treatment

Approximately 48 mL of an enzymatic treatment solution, containing the solid content of the hydrothermally treated rice straw obtained in Step 1 was prepared. Its composition is shown in Table 1.

TABLE 1

| enzyme treatment solution | approximately 48 mL |
|---|---|
| solid content of hydrothermally treated rice straw | 41.6 g (wet weight) |
| cellurase SS | 2.0 g |
| 1M citric buffer (pH 5.0) | 2.5 mL |
| 10XYP | 5.0 mL |

YP: yeast extract 10 g/L, polypeptone 20 g/L
celulase SS: Nagase Chemtex

This enzymatic treatment solution was put into a 50 mL plastic test tube (manufactured by Corning Incorporated) and then was rotated at a rotation rate of 35 rpm at 50° C. using a thermoblock rotator (SN-06BN, manufactured by Nissinrika) to perform the enzymatic treatment.

Step 3: First Cycle of Ethanol Fermentation

Yeast *Saccharomyces cerevisiae* TJ14 (Moukamnerd et. al., Appl. Microbiol. Biotechnol., 2010, vol. 88, p. 87-94) was used for the fermentation. Seed culture of the above-described yeast was performed in a test tube containing 5 mL of YPD liquid culture medium (10 g/L of yeast extract, 20 g/L of polypeptone and 20 g/L of glucose) overnight, and then, the culture medium was transferred into a flask containing 500 mL of YPD liquid culture medium and a main culture was performed for 2 days. This culture medium was centrifuged (3000 rpm, 4° C., 10 minutes), the yeast cells were washed twice with sterile distilled water, and then, the yeast cells were suspended in sterile distilled water so that its concentration was 100 g wet weight/L.

After 2 hours from the beginning of the enzymatic treatment in Step 2, 48 mL of the enzymatic treatment solution was transferred into a 80 mL screw-cap bottle (manufactured by Duran). Furthermore, 2 mL of the above-described yeast suspension was added thereto to set the concentration of the cells to 4 g wet weight/L. After the addition of the yeast, the fermentation was started at 37° C.

The concentrations of ethanol produced in the fermentation liquid were quantitated over time with an HPLC (High performance liquid chromatography system; Hitachi High-Tech Fielding Corporation, LaChrom Elite). ULTRON PS-80H (manufactured by Shinwa Chemical Industries Ltd., 300 mm (L)×8 mm (ID)) was used as a separation column for the HPLC, ultrapure water (water purified with Milli-Q manufactured by Millipore Japan Corporation) was used as a mobile phase, and a refractive index detector was used as a detector. The conditions of the HPLC included a flow rate of 0.9 mL/minute and a column temperature of 50° C.

Moreover, the concentrations of yeast cells in the fermentation liquid were quantitated over time by counting the number of colonies after spreading onto YPD agar culture medium (20 g/L of agar was added to YPD liquid culture medium) to culture at 30° C. for 2 days.

Step 4: Second Cycle of Ethanol Fermentation

After 48 hours from the beginning of the fermentation, the fermentation liquid was collected and was centrifuged at low rotation rate (100 G) with a centrifuge and thus was separated into precipitate (solid content; containing a large amount of lignin and an ash content) at 20% by mass and supernatant (liquid portion) at 80% by mass. Next, the supernatant was collected and was centrifuged at high rotation rate (1200 G) with a centrifuge and thus was separated into supernatant (liquid portion; containing ethanol) at 80% by mass and precipitate (solid content; containing a large amount of yeasts) at 20% by mass. The material balance of the fermentation liquid is shown in Table 2.

TABLE 2

| | ratio (mass %) | |
|---|---|---|
| | precipitate | supernatant |
| 1st centrifugal separation | 20 | 80 |
| 2nd centrifugal separation | 20 | 80 |

Next, the precipitate was collected, and was added to 48 mL of the enzymatic treatment solution obtained in the same manner as in Step 2 described above. The concentration of yeast cells was 1.5 g wet weight/L ($7.6 \times 10^6$ cells/mL: at the start of the second cycle of the ethanol fermentation). After the addition of the yeast, the fermentation was started at 37° C. in the same manner as in Step 3 described above. The concentrations of ethanol and yeast cells in the fermentation liquid were quantitated over time in the same manner as in Step 3. The concentration of yeast cells was 6.4 g wet weight/L ($3.2 \times 10^7$ cells/mL) at the end of the second cycle of the ethanol fermentation, and was increased from that at the start of the fermentation.

Step 5: Third to Sixth Cycles of Ethanol Fermentation

Step 4 was repeated four additional times in the same manner as described above. The results of the concentrations of ethanol produced in the fermentation liquid and yeast cells that were quantitated over time are shown in FIG. 1.

As is clear from FIG. 1, even when yeasts were reused and the fermentation was repeated from four to six times, the ethanol fermentation could be continued without problems. There was no need to supply additional yeasts prepared separately. It was found that the solid content containing yeasts after the end of each fermentation cycle is added to the fermentation liquid of the subsequent cycle at the ratio of 10 to 20% by mass with respect to the fermentation liquid, and thereby, ethanol fermentation can be performed for a long period of time while the concentration of yeast cells in the fermentation liquid is maintained in a certain range (approximately $10^6$ to $10^7$ cells/mL at the start of each fermentation cycle and $10^7$ cells/mL or more at the end of each fermentation cycle).

Example 2

Ethanol Fermentation Using Rice Straw 2

An experiment was performed in the same manner as in Example 1, except that a filtration separation was performed with a hydrasieve (0.1 mm screen; Toyo Screen Kogyo Co. Ltd.) instead of the centrifugation at a low rotation rate (100 G) using a centrifuge in Step 4 in Example 1. The collected supernatant (liquid portion) was 85% by mass.

Example 3

Ethanol Fermentation Using Rice Straw 3

An experiment was performed in the same manner as in Example 1, except that a micro separator (TSK-80 Basket Type Centrifuge; Σ: 31 m², bowl volume: 7 L, solid space: 4.8 L) was used for the centrifugation at an amount of supplied solution of 50 L/H instead of the centrifugation at a low rotation rate (100 G) with a centrifuge and a disk type centrifuge (LAPX 404 manufactured by Alfa Laval; Σ: 5230 m², bowl volume: 2.2 L, solid space: 1.1 L) was used for the centrifugation at an amount of supplied solution of 100 L/H instead of the centrifugation at a high rotation rate (1200 G) with a centrifuge. The supernatant (liquid portion) collected in the first centrifugation was 83% by mass. The precipitate (solid content) collected in the second centrifugation was 25% by mass. The concentration of yeast cells in each fraction is shown in Table 3.

TABLE 3

| fraction | viable cell number (number/mL) |
|---|---|
| supernatent of microseparator | 6.40E+06 |
| supernatent of disc type centrifuge | 3.30E+01 |
| precipitate of disc type centrifuge | 5.70E+07 |

As is clear from Table 3, the concentration of yeast cells in the supernatant (liquid portion) collected by the micro separator was $6.4 \times 10^6$ cells/mL, and there was almost no yeast in the supernatant (liquid portion) collected by the disk type centrifuge but there was a large amount of yeasts ($5.7 \times 10^7$ cells/mL) in the precipitate (solid content). As is clear from FIG. 1, this concentration of yeast cells in the solid content is such a concentration of yeast cells that allows for ethanol fermentation even when the solid content is added at a ratio of 10 to 20% by mass with respect to the fermentation liquid of the subsequent cycle. Accordingly, it was found that the yeast separated by the solid-liquid separation method of the above-described example is reused, and thereby, ethanol fermentation can be performed for a long period of time.

Example 4

Ethanol Fermentation Using Rice Straw 4

The ethanol fermentation was performed in the same manner as in Example 1, except that an enzymatic treatment solution was prepared by adding corn steep liquor (CSL) in the amount of 0.0625% by mass with respect to the total volume (mL) of the enzymatic treatment solution instead of 5.0 mL of 10×YP in Step 2 in Example 1.

Example 5

Ethanol Fermentation Using Rice Straw 5

Figure 2:
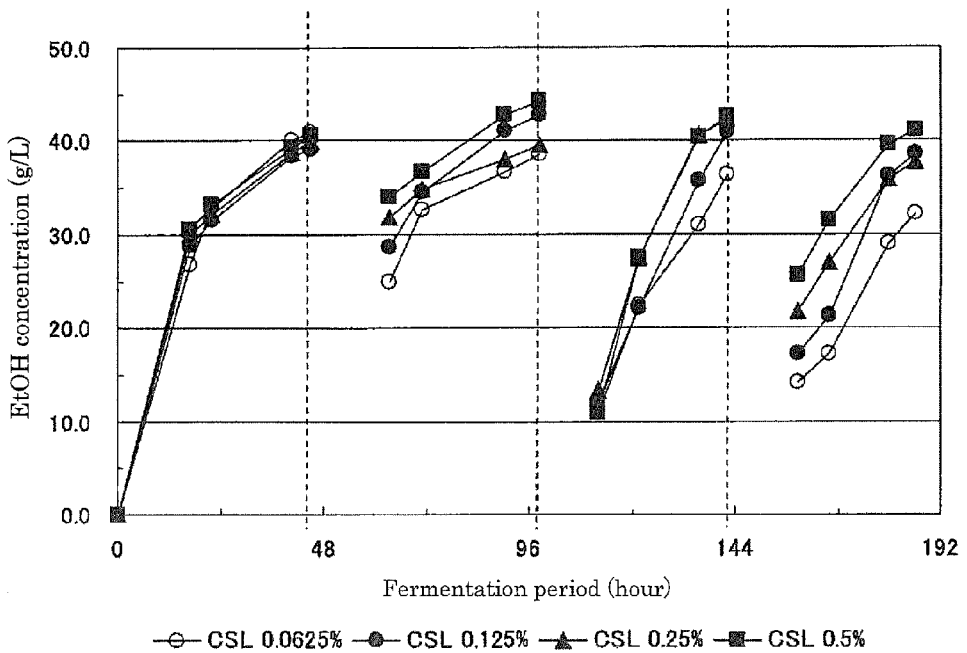
FIG. 2 is a graph illustrating time course in the concentration of ethanol in fermentation liquid in the case where rice straw was used as raw materials to perform ethanol fermentation with yeasts being repeatedly reused.

The ethanol fermentation was performed in the same manner as in Example 4, except that an enzymatic treatment solution was prepared by adding corn steep liquor in the amount of 0.125% by mass with respect to the total volume (mL) of the enzymatic treatment solution. The results of the concentrations of ethanol produced in the fermentation liquid that were quantitated over time are shown in FIG. 2.

Example 6

Ethanol Fermentation Using Rice Straw 6

The ethanol fermentation was performed in the same manner as in Example 4, except that an enzymatic treatment solution was prepared by adding corn steep liquor in the amount of 0.25% by mass with respect to the total volume (mL) of the enzymatic treatment solution. The results of the concentrations of ethanol produced in the fermentation liquid that were quantitated over time are shown in FIG. 2.

Example 7

Ethanol Fermentation Using Rice Straw 7

The ethanol fermentation was performed in the same manner as in Example 4, except that an enzymatic treatment solution was prepared by adding corn steep liquor in the amount of 0.5% by mass with respect to the total volume (mL) of the enzymatic treatment solution. The results of the concentrations of ethanol produced in the fermentation liquid that were quantitated over time are shown in FIG. 2.

As is clear from FIG. 2, when corn steep liquor was added in the amount of 0.125% by mass (Example 5), 0.25% by mass (Example 6) or 0.5% by mass (Example 7) with respect to the total volume (mL) of the enzymatic treatment solution, the ethanol fermentation could be performed stably even when the fermentation cycle was repeated. When corn steep liquor was added in the amount of 0.0625% by mass (Example 4) with respect to the total amount (mL) of the enzymatic treatment solution, the concentration of ethanol was reduced after the end of the third and fourth fermentation cycles, but the concentration of ethanol was not reduced after the end of the first and second fermentation cycles. As can be seen from this, the ethanol fermentation was performed sufficiently even when an inexpensive nutrient source such as corn steep liquor was used instead of an expensive nutrient source such as YP.

Example 8

Ethanol Fermentation Using Bagasse 1

Figure 3:
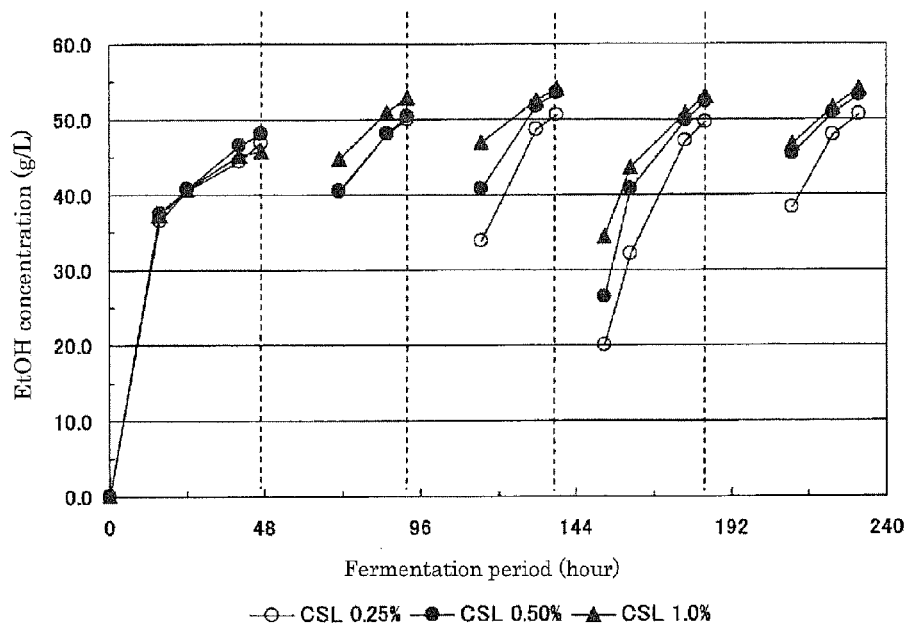
FIG. 3 is a graph illustrating time course in the concentration of ethanol in fermentation liquid in the case where bagasse was used as raw materials to perform ethanol fermentation with yeasts being repeatedly reused.

The ethanol fermentation was performed in the same manner as in Example 1, except that bagasse was used as a raw material instead of rice straw in Step 1 in Example 1 and that an enzymatic treatment solution was prepared by adding corn steep liquor in the amount of 0.25% by mass with respect to the total volume (mL) of the enzymatic treatment solution instead of 5.0 mL of 10×YP in the enzymatic treatment solution in Step 2 in Example 1. The results of the concentrations of ethanol produced in the fermentation liquid that were quantitated over time are shown in FIG. 3.

Example 9

Ethanol Fermentation Using Bagasse 2

The ethanol fermentation was performed in the same manner as in Example 8, except that an enzymatic treatment solution was prepared by adding corn steep liquor so that its content was 0.5% by mass with respect to the total amount (mL) of the enzymatic treatment solution. The results of quantitating the concentrations of ethanol over time produced in the fermentation liquid are shown in FIG. 3.

Example 10

Ethanol Fermentation Using Bagasse 3

The ethanol fermentation was performed in the same manner as in Example 8, except that an enzymatic treatment solution was prepared by adding corn steep liquor so that its content was 1% by mass with respect to the total volume (mL) of the enzymatic treatment solution. The results of quantitating the concentrations of ethanol over time produced in the fermentation liquid are shown in FIG. 3.

As is clear from FIG. 3, in the case of using bagasse as a raw material, the ethanol fermentation was also performed stably even when the fermentation cycle was repeated by adding corn steep liquor in the same manner as in Examples 4 to 7. Therefore, as can be seen the cost for producing ethanol could be reduced by using inexpensive corn steep liquor regardless of types of lignocellulosic biomass. It should be noted that bagasse have different components from those of rice straw, and thus the amounts of ethanol produced were different when using the same amount of corn steep liquor as compared with the results of Example 4.

Examples 11 to 14

Ethanol Fermentation Using Napier Grass

Step 1: Squeezing and Steaming Napier Grass

Napier grass was squeezed under a condition of 79.7 N·m with a single-axis extruder to remove the unnecessary liquid portion in advance, and the residue was impregnated with sulfuric acid at 1% by mass with respect to the residue and was steamed under a pressure of 1.0 MPa at 180° C. for 30 minutes. Next, the solid content was separated, and thus the separated solid content was used as a fermentation substrate.

Step 2: Enzymatic Treatment

1×YP, corn steep liquor at 1.0% by mass or 0.1% by mass (concentration with respect to the total volume of the enzymatic treatment solution), or water was used as a nutrient source in the enzymatic treatment solution to prepare four types of enzymatic treatment solutions, volumes of which were approximately 48 mL, containing the solid content of squeezed and steamed napier grass obtained in Step 1 (Examples 11 to 14). The compositions are shown in Table 4.

TABLE 4

| enzyme treatment solution | example 11 approximately 48 mL | example 12 approximately 48 mL | example 13 approximately 48 mL | example 14 approximately 48 mL |
|---|---|---|---|---|
| solid content of hydrothermally treated napier grass | 150 mg/mL (dry weight)*[1] | 150 mg/mL (dry weight)*[1] | 150 mg/mL (dry weight)*[1] | 150 mg/mL (dry weight)*[1] |
| celulase SS | 2.0 g | 2.0 g | 2.0 g | 2.0 g |

TABLE 4-continued

| enzyme treatment solution | example 11 approximately 48 mL | example 12 approximately 48 mL | example 13 approximately 48 mL | example 14 approximately 48 mL |
|---|---|---|---|---|
| 1M citric acid buffer (pH 5.0) | 2.5 mL | 2.5 mL | 2.5 mL | 2.5 mL |
| 1 × YP | 5.0 mL | — | — | — |
| corn steep liquor | — | 1.0%[*2] | 0.1%[*2] | — |
| water | — | — | — | 5.0 mL |

YP: yeast extract 10 g/L, polypeptone 20 g/L
celulase SS: Nagase Chemtex
[*1]dry weight (mg) to total amount of solution (mL)
[*2]concentration (%) to total amount of solution (mL)
—: no addition Each of these four types of enzymatic treatment solutions was put into a 50 mL plastic test tube (manufactured by Corning Incorporated) and then was rotated at a rotation rate of 35 rpm at 50° C. using a thermoblock rotator (SN-06BN, manufactured by Nissinrika) to perform the enzymatic treatment. Thereafter, ethanol fermentation was performed in the same manner as in Steps 3 to 5 in Example 1. The results of the concentrations of ethanol produced in the fermentation liquid that were quantitated over time are shown in FIG. 4.

Figure 4:
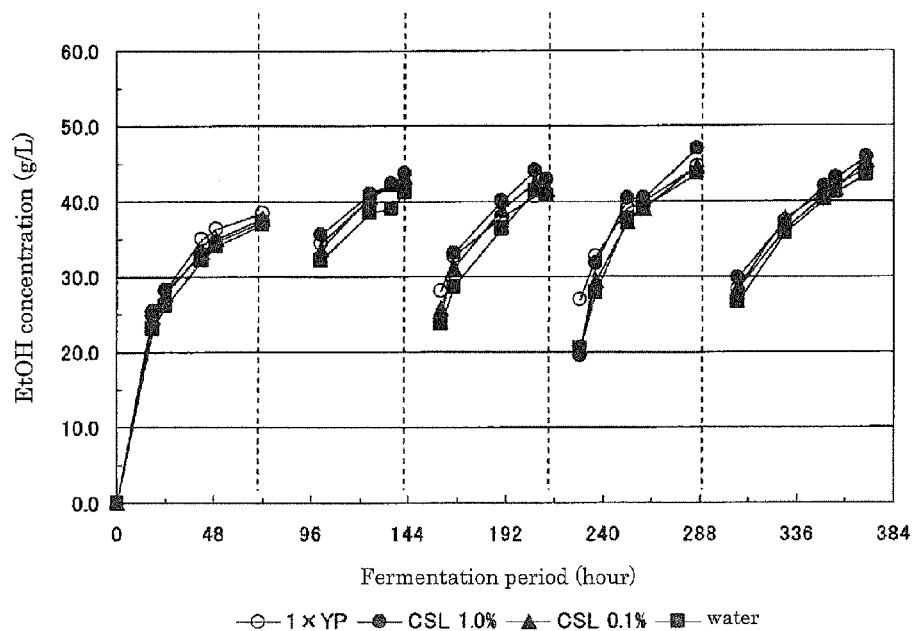
FIG. 4 is a graph illustrating time course in the concentration of ethanol in fermentation liquid in the case where napier grass was used as raw materials to perform ethanol fermentation with yeasts being repeatedly reused.

As is clear from FIG. 4, it was found that even when any of 1×YP (Example 11), corn steep liquor at 1.0% by mass (Example 12), corn steep liquor at 0.1% by mass (Example 13), and water (Example 14) is used as a nutrient source in the enzymatic treatment solution, ethanol was produced comparatively. As can be seen from this, when the solid content obtained by squeezing and steaming napier grass was used, the ethanol fermentation was stably performed without adding a nutrient source in every fermentation cycle of the alcohol fermentation.

Preparative Example 1

Production of a Yeast Displaying FaeA on its Surface

The plasmid pGK406AG (Japanese Laid-Open Patent Publication No. 2011-142879) was used as a plasmid including a promoter and a terminator necessary for a gene expression and an α-agglutinin gene that is necessary for the yeast surface display. Genome DNA was extracted from cultured cells of *Talaromyces funiculosus* in order to clone FaeA. PCR was performed using this genomic DNA as a template, and a primer SalI-ssFaeA-Fw (Sequence ID No. 1) including a secretion signal sequence of a glucoamylase gene derived from *Rhizopus oryzae*, and a primer SalI-FaeA-Rv (Sequence ID No. 2). The gene fragment obtained thereby was digested with SalI and thus the digestion product inserted into an SalI site of pGK406AG to construct a plasmid pGK406-ssFaeA-AG.

pAUR101 (manufactured by Takara Bio Inc.) was used as a vector for introducing a gene into a yeast. PCR was performed using the pGK406-ssFaeA-AG as a template, and primers pAuR101-SphI-Fw (Sequence ID No. 3) and pAuR101-SphI-Rv (Sequence ID No. 4) in order to insert a cassette including a pGK promoter, secretion signal sequence, FaeA and α-agglutinin of the pGK406-ssFaeA-AG constructed as described above into an SphI site of pAUR101. This gene fragment was inserted into the pAUR101 digested with SphI, using In-Fusion HD Cloning Kit (manufactured by Takara Bio Inc.), and thus a plasmid pAUR101-pGK-ssFaeA-AG for yeast surface display of FaeA was constructed. After cleaving this pAUR101-pGK-ssFaeA-AG with StuI, a yeast (*Saccharomyces cerevisiae* TJ14) was transformed with the cleaved product using YEAST MAKER Yeast Transformation System (Clontech Laboratories, Palo Alto, Calif., USA) to obtain an Aureobasidin A-resistant strain, and thus a yeast displaying FaeA on its surface was obtained. The obtained yeast displaying FaeA on its surface was used for the following Examples 15 and 16.

Example 15

Ethanol Fermentation Using a Yeast Displaying FaeA on its Surface 1

Step 1: Hydrothermal Treatment of Bagasse

Bagasse was mixed with water in the amount of approximately 20% by mass (dry mass). The mixture was put into a hydrothermal treatment device (manufactured by Mitsubishi Heavy Industries, Ltd.) and was treated at approximately 180° C. at approximately 3 MPa for 5 to 20 minutes. Then, a solid content was separated, and then, the separated solid content was used as a fermentation substrate.

Step 2: Enzymatic Treatment

Approximately 48 mL of an enzymatic treatment solution containing the solid content of the hydrothermally treated bagasse obtained in Step 1 was prepared. Its composition is shown in Table 5.

TABLE 5

| enzyme treatment solution | example 15 approximately 48 mL | example 16 approximately 48 mL |
|---|---|---|
| bagasse hydrothermal treatment solid content | 200 mg/mL (dry weight)[*1] | 150 mg/mL (dry weight)[*1] |
| celulase SS | 2.0 g | 2.0 g |
| 1M citric acid buffer (pH 5.0) | 2.5 mL | 2.5 mL |
| 10XYP | 5.0 mL | 5.0 mL |

YP: yeast extract 10 g/L, polypeptone 20 g/L
celulase SS: Nagase Chemtex
[*1]dry weight (mg) for total amount of solution (mL)

This enzymatic treatment solution was put into a 50 mL plastic test tube (manufactured by Corning Incorporated) and then was rotated at a rotation rate of 35 rpm at 50° C. using a thermoblock rotator (SN-06BN, manufactured by Nissinrika) to perform the enzymatic treatment.

Step 3: First Cycle of Ethanol Fermentation

Yeast displaying FaeA on its surface obtained in Preparative Example 1 was used for the fermentation. It should be noted that, ethanol fermentation was performed using a yeast *Saccharomyces cerevisiae* TJ14 as a control.

Seed culture of the above-described yeast was performed in a test tube containing 5 mL of YPD liquid culture medium (liquid culture medium containing 10 g/L of yeast extract, 20 g/L of polypeptone and 20 g/L of glucose) overnight, and then, the culture medium was transferred into a flask containing 500 mL of YPD liquid culture medium and a main culture was performed for 2 days. This culture medium was centrifuged (3000 rpm, 4° C., 10 minutes), the precipitated yeast cells were washed twice with sterile distilled water.

After 2 hours from the beginning of the enzymatic treatment in Step 2, 48 mL of the enzymatic treatment solution was transferred into an 80 mL screw-cap bottle (manufactured by Duran). Furthermore, the above-described yeast was added thereto to set the concentration of the cells to 20 g wet weight/L, and then, the fermentation was started at 37° C.

The concentrations of ethanol produced in the fermentation liquid were quantitated over time with an HPLC (Hitachi High-Tech Fielding Corporation, LaChrom Elite). ULTRON PS-80H (manufactured by Shinwa Chemical Industries Ltd., 300 mm (L)×8 mm (ID)) was used as a separation column for the HPLC, ultrapure water (water purified with Milli-Q manufactured by Millipore Japan Corporation) was used as a mobile phase, and a refractive index detector was used as a detector. The conditions of the HPLC included a flow rate of 0.9 mL/minute and a column temperature of 50° C. Moreover, the concentration of the yeast cells in the fermentation liquid was quantitated over time by counting the number of colonies after spreading onto YPD agar culture medium (20 g/L of agar was added to YPD liquid culture medium) to culture at 30° C. for 2 days.

Step 4: Second Cycle of Ethanol Fermentation

After 48 hours from the beginning of the fermentation, the fermentation liquid was collected, and was centrifuged at low rotation rate (100 G) with a centrifuge and thus was separated into precipitate (solid content; containing a large amount of lignin and an ash content) at 20% by mass and supernatant (liquid portion) at 80% by mass. Next, the supernatant was collected and was centrifuged at high rotation rate (1200 G) with a centrifuge, and thus was separated into supernatant (liquid portion; containing ethanol) at 80% by mass and precipitate (solid content; containing a large amount of yeasts) at 20% by mass.

Next, the precipitate was collected, and was added to 48 mL of the enzymatic treatment solution obtained in the same manner as in Step 2 described above. After the addition of the yeasts, the fermentation was started at 37° C. in the same manner as in Step 3 described above. The concentrations of ethanol and yeast cells in the fermentation liquid were quantitated over time in the same manner as in Step 3.

Step 5: Third to Fourth Cycles of Ethanol Fermentation

Figure 5:
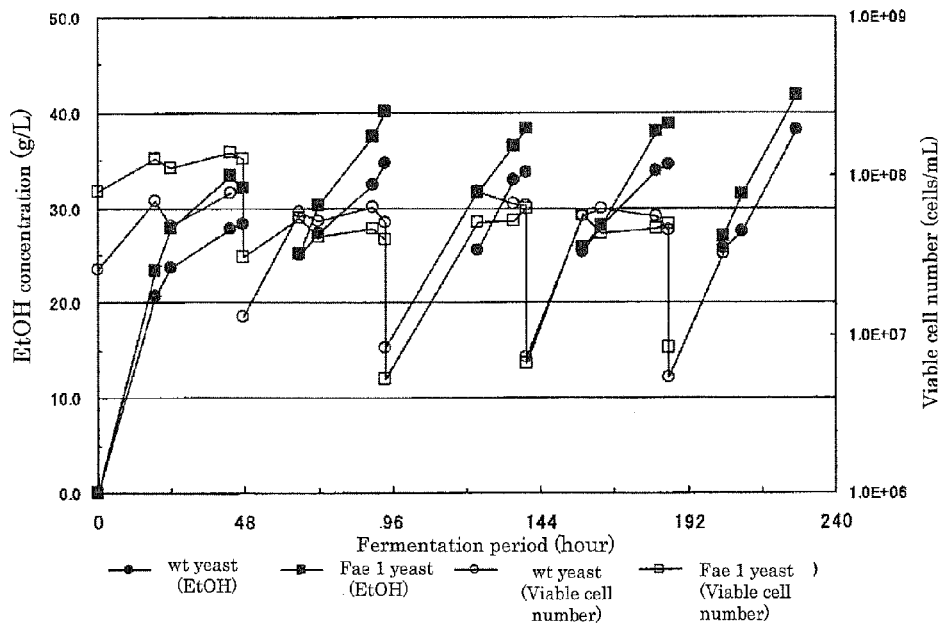
FIG. 5 is a graph illustrating time course in the concentrations of ethanol and yeast cells in fermentation liquid in the case where bagasse was used as raw materials to perform ethanol fermentation with FaeA-transformed yeasts being repeatedly reused.

Step 4 was repeated two additional times in the same manner as described above. The results of the concentrations of ethanol produced in the fermentation liquid and yeast cells that were quantitated over time are shown in FIG. 5.

Example 16

Ethanol Fermentation Using a Yeast Displaying FaeA on its Surface 2

Ethanol fermentation was performed using a yeast displaying FaeA on its surface and a control (a yeast *Saccharomyces cerevisiae* TJ14) in the same manner as in Example 15, except that an enzymatic treatment solution was prepared by adding the solid content of hydrothermally treated bagasse so as to make its concentration to 150 g/L (based on dry weight) (Table 5). The results of the concentrations of ethanol produced in the fermentation liquid and yeast cells that were quantitated over time are shown in FIG. 6.

Figure 6:
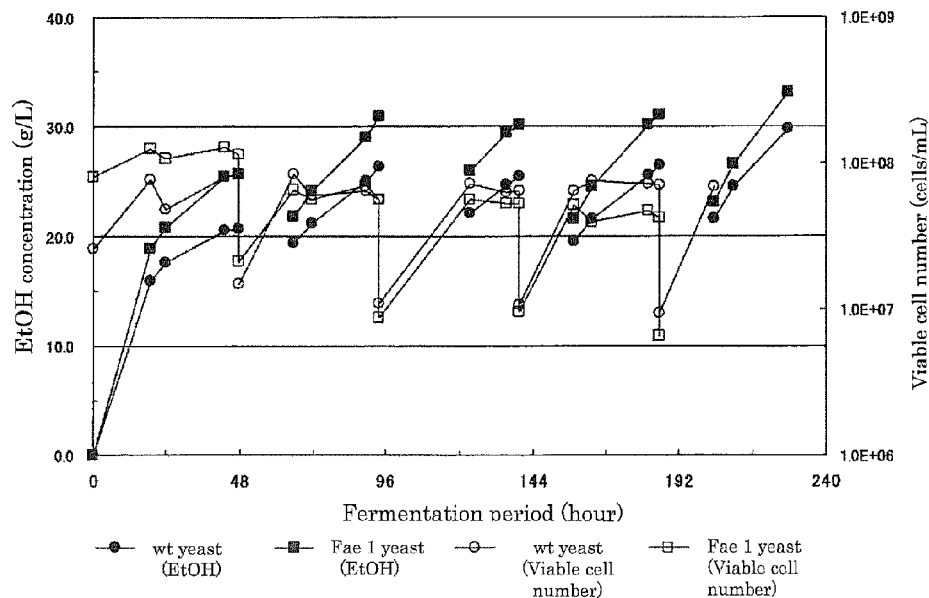
FIG. 6 is a graph illustrating time course in the concentrations of ethanol and yeast cells in fermentation liquid in the case where bagasse was used as raw materials to perform ethanol fermentation with FaeA-transformed yeasts being repeatedly reused.

As is clear from the results shown in FIGS. 5 and 6, it can be seen that when a yeast displaying FaeA on its surface was used, a larger amount of ethanol was stably produced compared with the wild-type yeast TJ14, using hydrothermally treated bagasse products at any of 200 g/L (Example 15) and 150 g/L (Example 16) based on dry weight. Moreover, it can be seen that a yeast displaying ferulic acid esterase on its surface promoted the saccharification of hydrothermally treated bagasse products with cellulase and produced a larger amount of ethanol than the wild-type yeast TJ14. Furthermore, it can be seen that ethanol fermentation could be performed for a long period of time while the concentration of yeast cells in the fermentation liquid was maintained in a certain range (approximately $10^6$ to $10^7$ cells/mL at the start of each fermentation cycle and $10^7$ cells/mL or more at the end of each fermentation cycle).

INDUSTRIAL APPLICABILITY

With the method of the present invention, by using, in the subsequent fermentation cycle, a certain amount of residue containing yeasts after removing a residue with a high specific gravity from the fermentation products of ethanol fermentation using lignocellulosic biomass, it is possible to repeat fermentation cycles for a long period of time without additionally supplying yeasts while the concentration of yeast cells is maintained in a certain range of approximately $10^6$ to $10^7$ cells/mL to $10^7$ cells/mL or more. Since yeasts constantly repeat proliferation, there is no problem in that its freshness is reduced. Since the cost for preparing a new batch of yeasts can be reduced, it is possible to produce ethanol at low cost. Moreover, it is possible to prevent the fermentation inhibition by the residue with a high specific gravity from inhibiting fermentation.

The invention claimed is:

1. A method for producing ethanol from lignocellulosic biomass, comprising steps of:
   (1) pretreating lignocellulosic biomass to obtain a water-insoluble cellulose fraction;
   (2) treating the water-insoluble cellulose fraction obtained in Step (1) with a cellulose hydrolase to obtain a saccharified biomass;
   (3) mixing the saccharified biomass obtained in Step (2) with yeasts to perform ethanol fermentation to obtain a fermented product; and
   (4) subjecting the fermented product obtained in Step (3) to a solid-liquid separation,
   the subjecting of Step (4) including steps of
      (a) removing a solid content constituting 5% to 30% by mass of the fermented product to obtain residues; and
      (b) collecting a solid content constituting 5% to 30% by mass of the residues,
   wherein a cycle including Steps (1), (2), (3) and (4) is repeated twice or more,
   wherein yeasts obtained in Step (4) are used as all or a portion of yeasts in Step (3) of a subsequent cycle, and
   wherein the yeast is transformed so as to express one or two enzymes selected from the group consisting of ferulic acid esterase, β-glucosidase, β-galactosidase and pectinase.

2. The method according to claim 1, wherein a concentration of yeast cells in the fermented product is $10^7$ cells/mL or more.

3. The method according to claim 2, wherein the enzyme is displayed on a yeast cell surface.

4. The method according to claim 1, wherein
   a concentration of yeast cells in the fermented product is $10^7$ cells/mL or more, and
   the fermented product contains the yeast, the ethanol, lignin and an ash content derived from the lignocellulosic biomass.

5. The method according to claim 4, wherein the enzyme is displayed on a yeast cell surface.

6. The method according to claim 1, wherein the enzyme is displayed on a yeast cell surface.

7. The method according to claim 1, wherein the saccharified biomass is in the form of a slurry.

* * * * *

SEQUENCE LISTING

```
<160> NUMBER OF SEQ ID NOS: 4

<210> SEQ ID NO 1
<211> LENGTH: 114
<212> TYPE: DNA
<213> ORGANISM: Artificial
<220> FEATURE:
<223> OTHER INFORMATION: SalI-ssFaeA-Fw

<400> SEQUENCE: 1
acgcgtcgac atgcaactgt tcaatttgcc attgaaagtt tcattctttc tcgtcctctc    60
```

```
ttactttct ttgctcgttt ctcagcaatc gctatggggc caatgcggtg gtac          114

<210> SEQ ID NO 2
<211> LENGTH: 38
<212> TYPE: DNA
<213> ORGANISM: Artificial
<220> FEATURE:
<223> OTHER INFORMATION: SalI-FaeA-Rv

<400> SEQUENCE: 2
acgcgtcgac gtggaataga gagaagaaac tccagatc                            38

<210> SEQ ID NO 3
<211> LENGTH: 36
<212> TYPE: DNA
<213> ORGANISM: Artificial
<220> FEATURE:
<223> OTHER INFORMATION: pAuR101-SphI-Fw

<400> SEQUENCE: 3
ctctgttgaa gcttggtaat acgactcact ataggg                              36

<210> SEQ ID NO 4
<211> LENGTH: 35
<212> TYPE: DNA
<213> ORGANISM: Artificial
<220> FEATURE:
<223> OTHER INFORMATION: pAuR101-SphI-Rv

<400> SEQUENCE: 4
gagtcgacct gcaggaatta accctcacta aaggg                               35
```